(12) United States Patent
Yamakawa et al.

(10) Patent No.: US 9,286,674 B2
(45) Date of Patent: Mar. 15, 2016

(54) OPHTHALMIC ANALYSIS APPARATUS AND OPHTHALMIC ANALYSIS PROGRAM

(71) Applicant: NIDEK CO., LTD., Gamagori, Aichi (JP)

(72) Inventors: Ai Yamakawa, Aichi (JP); Hisanori Torii, Aichi (JP); Norimasa Satake, Aichi (JP); Tetsuya Kano, Aichi (JP); Kenshiro Fujiu, Aichi (JP)

(73) Assignee: NIDEK CO., LTD., Aichi (JP)

( * ) Notice: Subject to any disclaimer, the term of this patent is extended or adjusted under 35 U.S.C. 154(b) by 2 days.

(21) Appl. No.: 14/161,734

(22) Filed: Jan. 23, 2014

(65) Prior Publication Data

US 2014/0205169 A1    Jul. 24, 2014

(30) Foreign Application Priority Data

Jan. 23, 2013  (JP) ................................. 2013-010642

(51) Int. Cl.
G06T 7/00       (2006.01)
A61B 3/10       (2006.01)
G01B 9/02       (2006.01)

(52) U.S. Cl.
CPC ............... *G06T 7/0012* (2013.01); *A61B 3/102* (2013.01); *G01B 9/02089* (2013.01); *G01B 9/02091* (2013.01)

(58) Field of Classification Search
CPC ............ G06T 7/0012; G06T 2207/10101; G06T 2207/20021; G06T 2207/20104; G06T 2207/30041; G06K 9/0061; G06K 2209/05; G01B 9/02083; G01B 9/02089; G01B 9/02091; A61B 3/102
See application file for complete search history.

(56) References Cited

U.S. PATENT DOCUMENTS

| 8,801,187 B1* | 8/2014 | Knighton et al. ...... A61B 3/102 |
| 2006/0159319 A1* | 7/2006 | Sathyanarayana ............ 382/128 |
| 2008/0204655 A1 | 8/2008 | Kikawa et al. ................ 351/206 |
| 2009/0123036 A1 | 5/2009 | Huang et al. .................. 382/117 |
| 2009/0123044 A1 | 5/2009 | Huang et al. .................. 382/128 |
| 2010/0238403 A1 | 9/2010 | Kobayashi et al. ............ 351/206 |
| 2011/0046480 A1 | 2/2011 | Yonezawa ..................... 600/425 |
| 2012/0127428 A1 | 5/2012 | Isogai et al. .................. 351/206 |
| 2012/0274898 A1 | 11/2012 | Sadda et al. ................... 351/206 |
| 2013/0182895 A1* | 7/2013 | Touzov et al. .......... G06T 11/003 |
| 2014/0112562 A1* | 4/2014 | Yamakawa et al. .. A61B 3/0025 |

FOREIGN PATENT DOCUMENTS

JP    2010246904 A    11/2010 .............. A61B 3/14

OTHER PUBLICATIONS

Extended European Search Report, dated May 9, 2014, issued by the European Patent Office in counterpart European Application No. 14152258.1.

* cited by examiner

*Primary Examiner* — Andrew W Johns
(74) *Attorney, Agent, or Firm* — Sughrue Mion, PLLC

(57) ABSTRACT

There is provided an ophthalmic analysis apparatus configured to acquire an analysis result of a tomographic image of a subject eye which is acquired by using optical coherence tomography (OCT), and to output the analysis result. The apparatus functions as a display control unit configured to control a display unit to display a two-dimensional image based on an OCT tomographic image; an analysis region setting unit configured to set multiple analysis regions on the two-dimensional image displayed on the display unit by the display control unit; and an output control unit configured to acquire an analysis result in the multiple analysis regions set by the analysis region setting unit and to output the acquired analysis result.

17 Claims, 7 Drawing Sheets

OPHTHALMIC ANALYSIS APPARATUS AND OPHTHALMIC ANALYSIS PROGRAM

CROSS-REFERENCE TO RELATED APPLICATION

This application claims priority from Japanese Patent Application No. 2013-010642, filed on Jan. 23, 2013, the entire subject matter of which is incorporated herein by reference.

TECHNICAL FIELD

The present disclosure relates to an ophthalmic analysis apparatus and an ophthalmic analysis program for analyzing a subject eye.

BACKGROUND

A tomographic image acquired by an ophthalmic optical coherence tomography (OCT) device is used in diagnosis of a subject eye. For example, in a case of an eye fundus OCT, a tomographic image of an eye fundus is acquired, and diagnosis is performed by the tomographic image itself, a thickness map or a thickness chart based on the tomographic image (refer to JP-A-2010-246904).

Incidentally, in the related art, a tomographic image displayed on a monitor is only displayed as an image. Therefore, an examiner evaluates a subject eye based on a result obtained by examining the tomographic image.

In addition, even when the tomographic image is output as a thickness map or a thickness chart, the examiner relies on analysis of the entire tomographic image. For this reason, the diagnosis using the tomographic image is not sufficiently performed.

SUMMARY

Accordingly, an aspect of the present disclosure provides an ophthalmic analysis apparatus which can output a useful analysis result.

According to an illustrative embodiment of the present disclosure, there is provided an ophthalmic analysis apparatus configured to acquire an analysis result of a tomographic image of a subject eye which is acquired by using optical coherence tomography (OCT), and to output the analysis result, the ophthalmic analysis apparatus comprising:
a processor; and
a memory storing computer readable instructions, when executed by the processor, causing the ophthalmic analysis apparatus to function as:
   a display control unit configured to control a display unit to display a two-dimensional image which is one of an OCT tomographic image, a two-dimensional front image whose position is associated with three-dimensional OCT data formed from an OCT tomographic image in each line, a two-dimensional analysis map which is calculated based on three-dimensional OCT data formed from an OCT tomographic image in each line, and a two-dimensional analysis chart which is calculated based on three-dimensional OCT data formed from an OCT tomographic image in each line;
   an analysis region setting unit configured to set multiple analysis regions on the two-dimensional image displayed on the display unit by the display control unit; and
   an output control unit configured to acquire an analysis result in the multiple analysis regions set by the analysis region setting unit and to output the acquired analysis result.

According to another illustrative embodiment of the present disclosure, there is provided a non-transitory computer-readable medium having a computer program stored thereon and readable by a computer configured to acquire an analysis result of a tomographic image of a subject eye which is acquired by using optical coherence tomography (OCT), the computer program, when executed by the computer, causing the computer to perform operations comprising:
   controlling a display unit to display a two-dimensional image which is one of an OCT tomographic image, a two-dimensional front image whose position is associated with three-dimensional OCT data formed from an OCT tomographic image in each line, a two-dimensional analysis map which is calculated based on three-dimensional OCT data formed from an OCT tomographic image in each line, and a two-dimensional analysis chart which is calculated based on three-dimensional OCT data formed from an OCT tomographic image in each line;
   setting multiple analysis regions on the two-dimensional image displayed on the display unit by the display control unit; and
   acquiring an analysis result in the multiple analysis regions set by the analysis region setting unit and outputting the acquired analysis result.

According to a further illustrative embodiment of the present disclosure, there is provided a method of controlling a ophthalmic analysis apparatus configured to acquire an analysis result of a tomographic image of a subject eye which is acquired by using optical coherence tomography (OCT), the method comprising:
   controlling a display unit to display a two-dimensional image which is one of an OCT tomographic image, a two-dimensional front image whose position is associated with three-dimensional OCT data formed from an OCT tomographic image in each line, a two-dimensional analysis map which is calculated based on three-dimensional OCT data formed from an OCT tomographic image in each line, and a two-dimensional analysis chart which is calculated based on three-dimensional OCT data formed from an OCT tomographic image in each line;
   setting multiple analysis regions on the two-dimensional image displayed on the display unit by the display control unit; and
   acquiring an analysis result in the multiple analysis regions set by the analysis region setting unit and outputting the acquired analysis result.

According to the above configuration, a useful analysis result can be output.

BRIEF DESCRIPTION OF THE DRAWINGS

The above and other aspects of the present disclosure will become more apparent and more readily appreciated from the following description of illustrative embodiments of the present disclosure taken in conjunction with the attached drawings, in which.

DESCRIPTION OF ILLUSTRATIVE EMBODIMENTS

Figure 1:
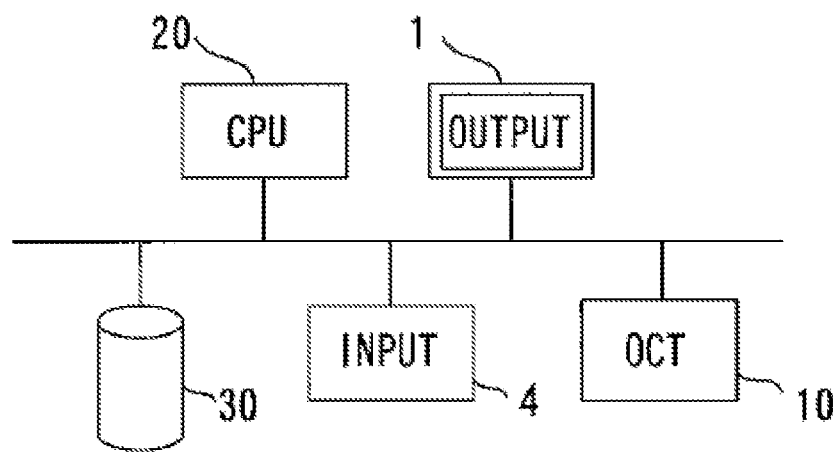
FIG. 1 is a block diagram showing a configuration of an eye fundus analysis apparatus according to an example.

An illustrative embodiment of the present disclosure will be described with reference to the drawings. FIGS. 1 to 16 are views according to illustrative embodiments of the present disclosure.

<Overview>

An ophthalmic analysis apparatus 100 acquires an analysis result of a tomographic image of a subject eye which is acquired by using an optical coherence tomography device 10. The ophthalmic analysis apparatus 100 outputs the acquired analysis result. The ophthalmic analysis apparatus 100 mainly includes a control unit 20 (refer to FIG. 1). The control unit 20 is, for example, connected to the optical coherence tomography device 10, a display unit 1, an input unit 4 and a storage unit 30, and performs a signal process.

As the tomographic image, for example, the tomographic image is acquired in which reflection intensity distribution in a depth direction of a tissue (for example, eye fundus or anterior ocular segment) of a subject eye is arrayed in a transverse direction. For example, the tomographic image is displayed in a state where one of vertical and horizontal directions on the display unit 1 is the transverse direction and the other is the depth direction.

As the analysis result, for example, either an analysis result of an eye fundus tomographic image or an analysis result of an anterior ocular segment tomographic image is used. For example, as the analysis result, an analysis result of the tomographic image of the entire eye from the cornea to the eye fundus may be used.

As the analysis result, for example, a thickness of the subject eye (for example, a thickness of the cornea, a thickness of the crystalline lens, and a thickness of at least one layer of the retina layers and choroid layer) and a curvature of the subject eye (for example, a curvature of the cornea, a front/rear curvature of the crystalline lens, and a curvature of at least one of the retina layers) are acquired. The analysis results are output as information of an analysis value (for example, an analysis parameter value of numeric data of thickness/curvature, a ratio of C (cup)/D (disk) of the eye fundus papilla), a measurement value of an anterior chamber angle (for example, ACD, TISA, ANGLE or the like), and lesion measurement information (for example, at least one of a size, an area and a volume). The analysis result may include an evaluation value obtained by segmenting the analysis value in a stepwise manner (for example, six stepwise evaluations of A to F). For example, in a case of the size of lesions, a lesion site is detected by image processing to measure any of the size, the area and the volume of the lesions.

The control unit 20 operates, for example, as a display control unit. That is, the control unit 20 may display the tomographic image acquired by the optical coherence tomography device 10, on the display unit 1.

The control unit 20, for example, operates as an analysis region selection unit (hereinafter, referred to as a region selection unit). The control unit 20 may select multiple analysis regions with respect to the tomographic image displayed on the display unit 1. Here, it is possible to appropriately evaluate a tomographic image by setting the multiple analysis regions with respect to the same tomographic image displayed in a certain image display region on the display unit 1.

When selecting the multiple analysis regions, the control unit 20 may select a first analysis region and a second analysis region which is different from the first analysis region, on the same tomographic image. The first analysis region and the second analysis region may be separated from each other. In this case, for example, it is possible to acquire the analysis result of mutually separated regions on the tomographic image. Alternatively, the first analysis region and the second analysis region may be continued to each other. In this case, for example, it is possible to acquire the analysis result of mutually continued regions on the tomographic image. Of course, the first analysis region and the second analysis region may be partially overlapped with each other.

The control unit 20 operates, for example, as an analysis result output unit. That is, the control unit 20 may acquire the analysis result in the selected multiple analysis regions, and may output the acquired analysis result.

The storage unit 30 may be, for example, a storage unit provided in a device body of the optical coherence tomography device 10, a storage unit provided in an external server, or a storage unit provided in a personal computer. Of course, a storage unit which stores an eye fundus analysis program and a storage unit which stores analysis results may be provided separately, or may be configured by the same device.

The control unit 20 operates, for example, as an instruction receiving unit that receives an instruction from an examiner. That is, the control unit 20 may receive an operation signal from a user interface (operation input unit) such as a touch panel, a mouse, a keyboard and the like.

The control unit 20 operates, for example, as an input receiving unit that receives an input from an examiner and a part of the apparatus. That is, the control unit 20 may receive an operation signal from the input unit 4 (for example, the user interface such as the touch panel, the mouse, the keyboard and the like). The input receiving unit may receive, for example, data from the storage unit 30 storing various information.

The control unit 20 operates, for example, as a characteristic site detection unit that detects a characteristic site in the tomographic image through image processing. That is, the control unit 20 detects, for example, at least one of the macula, fovea centralis, papilla, blood vessel, a lesion site and the like of the eye fundus of the subject eye by using a detection algorithm. As the detection algorithm, an algorithm which detects a characteristic site by utilizing image features of the characteristic site (for example, brightness, a shape, a thickness and the like) may be used.

The control unit 20 may detect the characteristic site in the tomographic image by associating positional information of the characteristic site which is acquired by using an examination result of a perimeter or an analysis result of a front image captured by an eye fundus camera or an SLO, with the tomographic image. That is, the control unit 20 may have any configuration which can detect the characteristic site in the tomographic image.

<Selection of Analysis Region for Tomographic Image>

As a region to be selected by the instruction receiving unit, for example, a one-dimensional region or a two-dimensional region on the tomographic image (refer to FIG. 2) can be selected. For example, as the one-dimensional region, an analysis result relating to a depth direction is selected by setting one line in the depth direction. Of course, at least a portion of a line in the other direction (for example, a line in a transverse direction) may be selected. The line may be a line extending from one end to the other end of an image, or may be a portion thereof.

As the two-dimensional region, for example, an analysis result relating to a depth direction at multiple positions may be selected by setting a region formed from multiple A scanning lines in the depth direction. The A scanning line may be an A scanning line extending from one end to the other end of an image, or may be a portion thereof. The same is applied to a region which is set with respect to the transverse direction.

When setting a follow-up observation position for the one-dimensional region on the tomographic image, for example, the control unit 20 may receive a selection instruction from an examiner in order to select the one-dimensional region on the tomographic image which is output onto a display screen of the display unit 1, as a graph creation region. For example, the control unit 20 may acquire at least one analysis result in the selected one-dimensional region. Accordingly, for example, a time-series graph relating to the one-dimensional region on the tomographic image selected by the examiner is output.

For example, a movable line (straight line, line segment) is displayed to be superimposed on the tomographic image, and the one-dimensional region designated by the line is selected as the graph creation region. That is, the selected one-dimensional region may be displayed to be distinguishable by being displayed in a display mode which is different from that of the other regions. For example, the selected one-dimensional region may be displayed in the different display mode (for example, a different color, and different contrast). Further, two arbitrary points may be designated on the tomographic image such that a region connecting two points is selected.

When setting a follow-up observation position for the two-dimensional region on the tomographic image, for example, the control unit 20 may receive a selection instruction from an examiner in order to select the two-dimensional region on the tomographic image which is output onto the display screen of the display unit 1, as the graph creation area. For example, the control unit 20 may acquire at least one analysis result in the selected two-dimensional region. Accordingly, for example, a time-series graph relating to the two-dimensional region on the tomographic image selected by the examiner is output (refer to FIG. 10).

For example, a movable frame is displayed to be superimposed on the tomographic image, and the two-dimensional region designated by the frames is selected as the graph creation region. Here, a shape of the frames is not limited to a rectangular shape, and any desired shape (for example, a circular shape) can be used. That is, the selected two-dimensional region may be displayed to be distinguishable from the other regions. For example, the selected two-dimensional region may be displayed in a different display mode (for example, a different color, and different contrast).

Further, two arbitrary points may be designated on the tomographic image and the two-dimensional region whose diagonal line is a line segment connecting two points may be selected as the analysis region.

When acquiring at least two analysis regions in the two-dimensional region, for example, the control unit 20 may acquire the analysis result by integrating multiple analysis results. As an integrated result, basic statistics may be used. The basic statistics may be a representative value (mean, median, mode, maximum value, minimum value or the like), a degree of dispersion (dispersion, standard deviation or coefficient of variation), and the like.

The control unit 20 may acquire the representative value (for example, the mean) of the analysis result for respective A scanning signals in the two-dimensional region, or may acquire the maximum value/minimum value in the two-dimensional region.

<Selection of Multiple Analysis Regions for Tomographic Image>

The control unit 20 may, for example, as the instruction receiving unit, receive a selection instruction from the examiner in order to select multiple analysis regions on the tomographic image. Then, the control unit 20 selects the multiple analysis regions for the tomographic image in accordance with the received selection instruction. Accordingly, for example, the examiner can select the multiple desired analysis regions for the tomographic image. As long as the control unit 20 selects multiple analysis regions, the control unit 20 may select two, three or more analysis regions.

In addition to the first analysis region and the second analysis region which are associated with each other, a third analysis region and a fourth analysis region which are associated with each other may be selected. In this case, for example, when multiple abnormal sites are formed, it is possible to acquire the analysis result in the multiple analysis regions relating to a first abnormal site, and to acquire the analysis result in the multiple analysis regions relating to a second abnormal site. In this case, an integrated result relating to the first analysis region and the second analysis region, and an integrated result relating to the third analysis region and the fourth analysis region may be respectively acquired.

Figure 2:
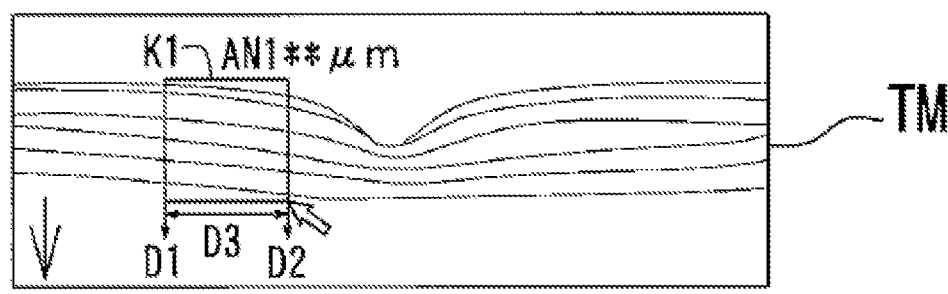
FIG. 2 shows an example for two-dimensionally setting an analysis region on a tomographic image according to an example.
Figure 3:
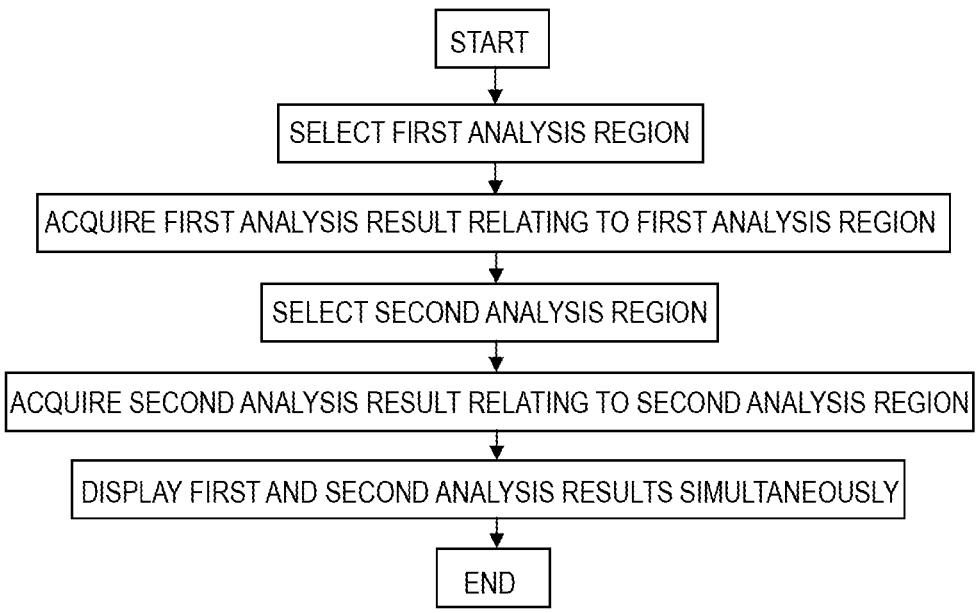
FIG. 3 is a flowchart showing an exemplary flow when selecting multiple analysis regions on a tomographic image.
Figure 4:
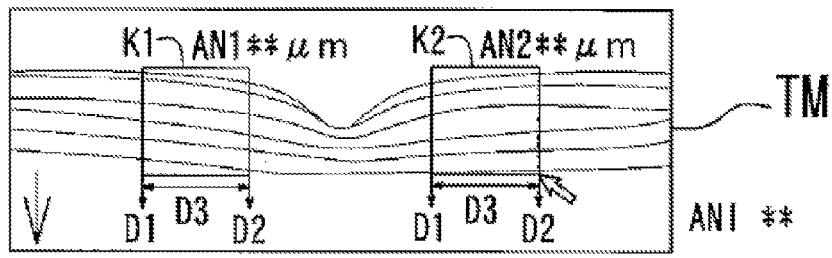
FIG. 4 shows an example when setting a second analysis region according to an example.

That is, the control unit 20 may display patterns for defining each analysis region in a region corresponding to the selection instruction received by the instruction receiving unit (for example, refer to FIGS. 2 to 4). The patterns are displayed to be superimposed on the tomographic image displayed on the display unit 1. Then, the control unit 20 selects the multiple analysis regions based on a display region of each pattern on the tomographic image. According, for example, it is possible to easily select the analysis regions on the tomographic image.

The control unit 20 may cause a first pattern for defining the first analysis region and a second pattern for defining the second analysis region to be simultaneously displayed on the display unit 1. The control unit 20 may perform the definition using the first pattern and the definition using the second pattern at different times, and may consequently select the first analysis region and the second analysis region. The control unit 20 may perform the definition using the first pattern and the definition using the second pattern at the same time, and may simultaneously select the first analysis region and the second analysis region.

The selection of the analysis region is not limited to the selection instruction from the examiner. For example, a position of the analysis region on the tomographic image may be set based on a position of a characteristic site detected by the control unit 20. Accordingly, for example, positional setting of the analysis region is facilitated, thereby enabling analysis work to be smoothly performed.

In this case, the control unit 20 may determine the position of the analysis region based on the position of the characteristic site. The control unit 20 may display indication (for example, highlighting, a mark display or the like) of the position of the characteristic site on the tomographic image displayed on the display unit 1 in order to assist the selection instruction of the examiner.

<Position and Size of Analysis Region>

The control unit 20 may change at least any of a position, a size and a shape of the analysis region with respect to the tomographic image. That is, for example, since the position, the size and the shape can be changed, it is possible to acquire the analysis result in any desired analysis region.

The control unit 20 may be configured to pre-set at least any one of the position, the size and the shape of the analysis region with respect to the tomographic image, and to select the multiple analysis regions at a pre-set position or in a pre-set size. Accordingly, for example, the analysis region can be selected in a state where the position, the size and the shape are pre-set, so that it is possible to easily acquire the analysis result in the analysis region desired by the examiner.

<Reference Position Setting>

Figure 5:
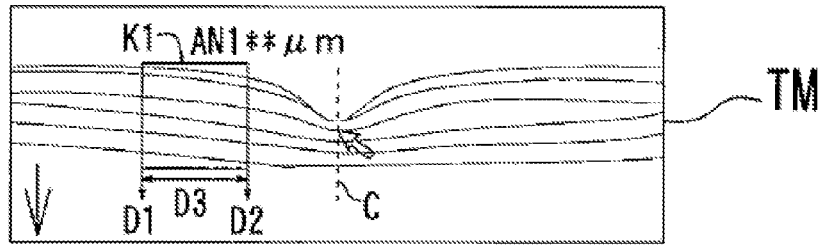
FIG. 5 shows an example when setting a center position on a tomographic image.
Figure 6:
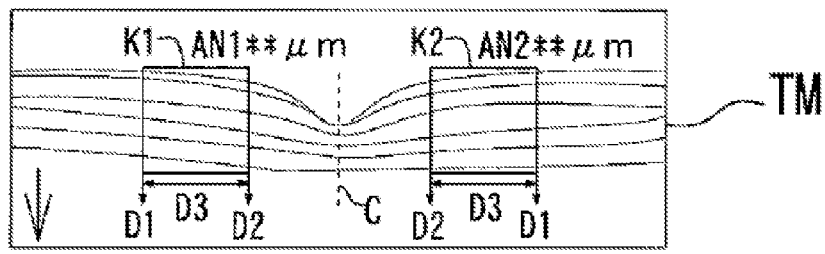
FIG. 6 shows an example when setting a second analysis region based on a first analysis region and the center position.
Figure 7:
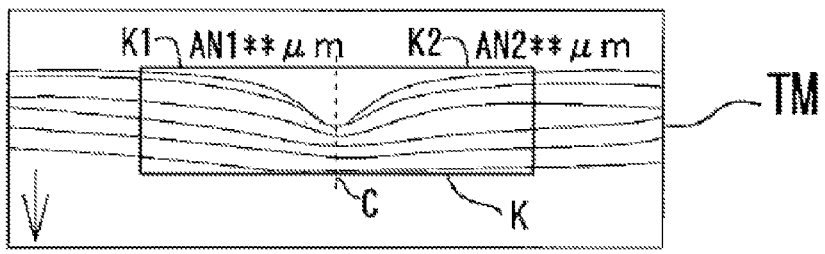
FIG. 7 shows an example when dividing an analysis region based on the center position.

The control unit 20 may be configured to set a reference position among multiple selected analysis regions on the tomographic image (for example, refer to FIGS. 5 to 7). For example, the control unit 20 may be configured to select the first analysis region and the second analysis region which are symmetric to each other with respect to the reference position. Accordingly, for example, it is possible to easily determine symmetricity in the multiple analysis results.

The control unit 20 may, for example, set the position of the second analysis region based on the pre-set first analysis region and the reference position (refer to FIGS. 5 and 6). Accordingly, for example, the effort of setting the second analysis region is reduced.

The control unit 20 may, for example, divide the pre-set analysis region based on the reference position, and may set the divided analysis regions as the first analysis region and the second analysis region (refer to FIG. 7).

The control unit 20 may set the reference position on the tomographic image in accordance with the instruction received by the control unit 20 (instruction receiving unit). For example, patterns (refer to C in FIGS. 5 to 7) for defining the reference position are displayed to be superimposed on the tomographic image of the display unit 1.

The setting of the reference position is not limited to that based on the selection instruction from the examiner. For example, the reference position may be set on the tomographic image based on the position of the characteristic site detected by the control unit 20. Accordingly, for example, the setting of the reference position is facilitated.

The control unit 20 may, for example, set each analysis region at a position which is symmetric with respect to the reference position. In addition, the control unit 20 may set each analysis region at a position rotated about the reference position. Further, for example, the control unit 20 may set the first analysis region at a position separated from the reference position by a first distance, and may set the second analysis region at a position separated from the reference position by a second distance which is different from the first distance.

<Output of Analysis Result>

When outputting the analysis result relating to the multiple analysis region, for example, at least any of the analysis result in each analysis region and the integrated analysis result of the respective analysis results (ratio, difference or the like) is output.

When acquiring the analysis result of a region selected as the analysis region, the control unit 20 can reduce a processing period of time, for example, by acquiring the analysis result acquired in advance with respect to the selected region.

A coordinate position of the tomographic image may be associated with the analysis result at the coordinate position in advance. When acquiring the analysis result acquired in advance, the control unit 20 may, for example, acquire the analysis result corresponding to a specified coordinate position if the coordinate position of the tomographic image corresponding to the selected analysis region is specified. Of course, when the analysis region is selected, the control unit 20 may analyze the tomographic image and acquire the analysis result relating to the selected region.

An output destination may include, for example, an output unit (output device) such as a display unit (for example, the display unit 1) or a printer, and a storage unit (storage device) such as a hard disk or a USB memory. In a case of the display unit, the analysis result is displayed on a monitor, and in a case of the printer, the analysis result is printed. In a case of the storage unit, the analysis result stored in the storage unit can be output to the output unit.

A device of the output destination may have, for example, at least any of a configuration mounted on the optical coherence tomography device, a configuration externally attached to the optical coherence tomography device, and a configuration arranged at a position separated from the optical coherence tomography device.

<Time-Series Graph>

Figure 10:
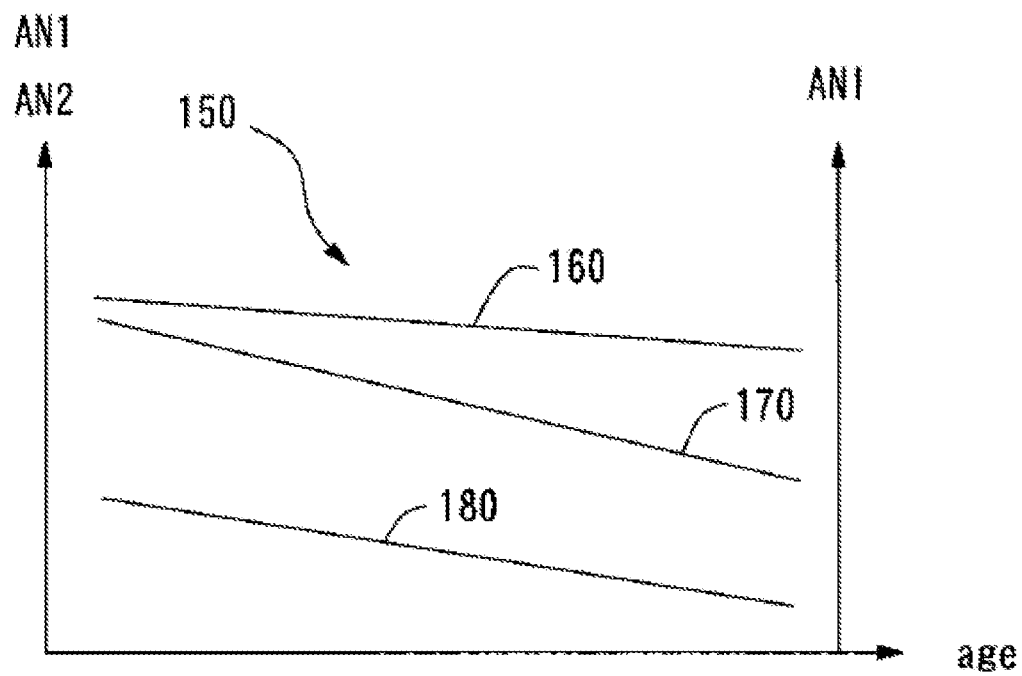
FIG. 10 shows an example when outputting a time-series graph by using analysis results for multiple analysis regions.

The control unit 20 (for example, CPU 20) may acquire time-series data of the analysis result from the storage unit 30 and may output a time-series graph based on the time-series data (refer to FIG. 10). The storage unit 30 stores the analysis results of the tomographic image of the subject eye which are acquired on different days.

Data output by the control unit 20 is not limited to the time-series data, and may be any statistical information (for example, a numeric value and a chart) formed from the time-series data of the analysis result. The statistical information may be a statistical result in which distribution of the analysis results is summarized in a time-series manner such that characteristics of the time-series data can be recognized. As the statistical information, it is preferable that the statistical results be expressed by the numeric value or the chart.

The control unit 20 may, for example, acquire a regression line by a regression analysis of the time-series data, and may output a trend graph based on the regression line as the time-series data. The control unit 20 may, for example, output a gradient of the acquired regression line or a p-value. The control unit 20 may acquire a regression curve by the regression analysis, and may output a trend graph based on the regression curve.

<Example>

Hereinafter, an example of the illustrative embodiment will be described in detail with reference to the drawings. In the following description, as the ophthalmic analysis apparatus, an eye fundus analysis apparatus will be described as an example.

FIG. 1 is a block diagram showing a configuration of the eye fundus analysis apparatus according to the example. As shown in FIG. 1, this apparatus include the control unit 20 operating as a processor which performs arithmetic processing for the overall eye fundus analysis apparatus, the storage unit 30, the display unit 1, and the input unit 4. Each unit is electrically connected to the control unit 20 via a bus.

The storage unit 30 is a non-volatile memory. The storage unit 30 is a non-transitory storage medium which can store contents even when a power supply is off. For example, a hard disk drive, a flash ROM, and a USB memory which is detachably attached to the ophthalmic analysis apparatus can be used as the storage unit 30. An eye fundus analysis program for analyzing the eye fundus of the subject eye is stored in the storage unit 30.

The eye fundus analysis program may be installed in a commercially available personal computer (PC) to operate as the control unit 20, the input unit 4, the storage unit 30 and the display unit 1, by using an arithmetic processing unit, an input unit, a storage unit and a display unit of the commercially available PC. Of course, as the control unit 20, the input unit 4, the storage unit 30 and the display unit 1, an arithmetic unit, an input unit, a storage unit and a display unit included in the optical coherence tomography device 10 may be used.

The display unit 1 displays the tomographic image acquired by the ophthalmic optical coherence tomography device, the analysis result of the tomographic image, and the time-series graph formed from the time-series data of the acquired analysis result, on the display screen. The input unit 4 has the keyboard, the mouse and the like, and is configured such that a user of the eye fundus analysis apparatus can inputs various information.

For example, the eye fundus analysis apparatus of the present example is a computer. The control unit 20 executes a program by performing various arithmetic processes after reading out the eye fundus analysis program on a RAM. For example, the control unit 20 controls the display screen of the display unit 1 according to the eye fundus analysis program.

The storage unit 30 stores, for example, the analysis result of the tomographic image of the subject eye by using the optical coherence tomography device 10. For example, the analysis results acquired on different days include forming results for each subject person who is a follow-up observation target and forming results for each examination day.

The storage unit 30 may store, for example, in addition to the analysis results, the reference tomographic image from which the analysis result is acquired, a layer thickness map image based on the analysis result (for example, thickness map image), a scan pattern used when acquiring the tomographic image, a scanning position and the like. The data is appropriately converted into image data by the control unit 20, and is presented to a user via the display screen of the display unit 1.

The storage unit 30 may store, for example, information relating to events. The information relating to the events may include, for example, information relating to the events of retinal treatment. The storage unit 30 may store, for example, a date of the event and a type of the event (for example, medication and surgery (photocoagulation, TTT, PDT or the like)) for each subject person. The storage unit 30 may store a scheduled date of the event in the future and the type of the event.

The storage unit 30 may, for example, store a normal eye database. The normal eye database may store, for example, a database which stores a retinal thickness of the normal eye relating to a retinal disease, based on the examination results obtained from the eye of multiple patients and the prescription results. The normal eye database is created, for example, in a state where the disease is not specified and the retinal thickness or a retinal slope is classified as normal or abnormal. Of course, the normal eye database may be created for each specific disease. In addition, a normal eye database relating to myopia may be created.

The optical coherence tomography (OCT) device 10 is a device which acquires the tomographic image of the eye fundus of the subject eye. Based on the acquired tomographic image, the analysis result relating to the eye fundus of the subject eye (for example, information of the retinal thickness) is acquired. With regard to a function for acquiring the analysis result by analyzing the tomographic image, the control unit which controls the optical coherence tomography (OCT) device 10 may analyze the tomographic image. Alternatively, another control unit may analyze the tomographic image acquired by the optical coherence tomography (OCT) device 10.

The optical coherence tomography device 10 splits a light beam emitted from a light source into a measurement light and a reference light. Then, the optical coherence tomography device 10 guides the split measurement light to an eye fundus Ef of an eye E, and guides the split reference light to a reference optical system. Thereafter, an interference light of the measurement light reflected on the eye fundus Ef and the reference light is received by a detector (light receiving element). The detector detects an interference state between the measurement light and the reference light. In a case of Fourier-domain OCT, spectral intensity of the interference light is detected by the detector, and a depth profile within a predetermined range is acquired by performing Fourier transform on spectral intensity data. The Fourier-domain OCT includes spectral-domain OCT (SD-OCT) and swept-source OCT (SS-OCT). In addition, the optical coherence tomography device 10 may be a time-domain OCT (TD-OCT) device.

The optical coherence tomography (OCT) device 10 may have a front observation optical system for acquiring the front image of the eye fundus of the subject eye. The front observation optical system may be a scanning type confocal optical system or an eye fundus camera optical system. The front image of the eye fundus may be acquired based on an interference signal acquired by the optical coherence tomography device 10.

The optical coherence tomography device 10 acquires the tomographic image of the eye fundus Ef based on an output signal from the detector. For example, the acquired tomographic image is subjected to image processing, and the retinal thickness of the eye fundus Ef is measured. As the retinal thickness, for example, a thickness of each layer of the retina (specifically, a thickness of an optic nerve fiber layer (NFL), a thickness from an inner limiting membrane (ILM) to a retinal pigment epithelium (RPE) or the like) is acquired.

Of course, the two-dimensional retinal thickness information (thickness map) may be subjected to follow-up observation. The acquired retinal thickness information is sent to the control unit 20 and is stored in the storage unit 30. In addition, the storage unit 30 stores image information acquired by the optical coherence tomography device 10 (tomographic image of the eye E, front image and the like), an analysis chart calculated based on the thickness information, various parameters and the like.

The thickness of the choroid layer may be measured by processing the acquired tomographic image. Of course, the two-dimensional choroid layer information (thickness map) may be subjected to follow-up observation.

If a periodic examination is performed by using the optical coherence tomography device 10, the retinal thickness information acquired on different days as a result of the follow-up observation is sent to the control unit 20, and then is stored in the storage unit 30. For example, the retinal thickness information stored in the storage unit 30 is stored in association with a time axis for the follow-up observation. The retinal thickness information as a function of time represents a time-dependent change of the retinal thickness.

A time interval for implementing the periodic examination is generally every one month to every three months. For example, the retinal thickness information is stored on a monthly basis. The information of the time-dependent change is output to the display unit 1 in a form of the graph as shown in FIG. 10.

The event information relating to the subject eye (for example, a type of treatment for subject eye E, the treatment date and the like) is stored in the storage unit 30 via the input unit 4. An input method of the event information may include selection of the type/examination date through a pull-down menu on the display unit 1, and a direct input using the keyboard. The event information is, for example, output onto the graph of the display unit 1.

The storage unit 30 stores examination data acquired by using other devices in addition to the optical coherence tomography device 10, via the input unit 4. For example, the examination information acquired by the other devices includes vision examination results, visual-field examination results, images captured by using the eye fundus camera, and the like. An input method of the examination data by using the other devices includes selection of the type/examination date through a pull-down menu on the display unit 1, and the direct input using the keyboard.

The optical coherence tomography (OCT) device 10 and the eye fundus analysis apparatus are connected to each other in a state where a signal is exchangeable. Various data acquired by the optical coherence tomography (OCT) device 10 (for example, tomographic image data, front image data, various photographing conditions when acquiring the image (for example, scanning position of the measurement light and the examination date) and the like) are stored in the storage unit 30.

<Area Setting in Multiple Regions on Tomographic Image>

FIG. 2 is a view for two-dimensionally setting the analysis region on the tomographic image. For example, the control unit 20 electronically displays a frame K1 on a tomographic image TM displayed in a predetermined display region on the display unit 1. The frame K1 is displayed on the tomographic image TM by a predetermined operation. For example, in a state where one arbitrary point is designated on the tomographic image TM, the frame K1 is displayed by a drag operation in an oblique direction.

The control unit 20 receives an operation signal from the input unit 4, and adjusts a size and a display position of the frame K1 on the tomographic image TM. The frame K1 is used, for example, in setting an arbitrary area (two-dimensional region) on OCT data. The frame K1 is displayed, for example, so as to surround at least a portion of the region on the tomographic image TM, and is used in acquiring layer thickness data inside a specific area in the tomographic image TM. As long as the arbitrary area can be set on the OCT data, for example, the area may be designated by a click operation of the mouse or by a touch operation on the touch panel. Further, as long as an area can be set on the tomographic image TM, the displayed shape of the frame K1 is not limited to the shape shown in FIG. 2.

FIG. 3 is a flowchart showing an exemplary flow when selecting multiple analysis regions on a tomographic image.

For example, after a start point of the analysis region is designated by the input unit 4, when a cursor on the tomographic image TM is moved by the examiner's operation, the control unit 20 changes the size of the frame K1 in the vertical and horizontal directions in accordance with a movement position thereof (refer to FIG. 2).

The control unit 20 sets a first area set via the input unit 4 as the first analysis region. That is, the first analysis region is set by the frame K1. Then, the control unit 20 displays a first analysis result AN1 relating to the first analysis region on the tomographic image TM.

Then, the control unit 20 acquires multiple layer thickness data included in the area set by the first frame K1. The control unit 20 calculates a basic statistical value of the respective layer thickness data inside the area (for example, a representative value, a degree of dispersion, more specifically, a mean of layer thickness data, and the like). In the retinal layer inside the area, with regard to the retinal layer for outputting the layer thickness data, a start end layer and a terminal end layer are set in advance in an analysis layer selection region (not shown) displayed on the display unit 1.

The control unit 20 displays the basic statistical value of the acquired layer thickness data to be superimposed on the tomographic image TM as the first analysis result AN1. In addition to the basic statistical value, the control unit 20 may display a first distance D1, a second distance D2 and an analysis width D3 which relate to a scanning direction (transverse direction) on the tomographic image TM by using actual dimensions. The first distance D1 is a distance from the start point of the scanning to the start point of the analysis region. The second distance D2 is a distance from the start point of the scanning to the terminal point of the analysis region. The analysis width D3 is a distance from the start point to the terminal point in the scanning direction, and represents the analysis width of the analysis region.

The control unit 20 displays the first analysis result AN1 in real time in response to the frame K1 changed by the examiner. Then, when receiving an input signal for completing the adjustment of the frame K (for example, completion of the drag operation), the control unit 20 temporarily completes an analyzing process in real time. Then, the control unit 20 fixedly displays the first analysis result AN1 corresponding to the first analysis region.

Furthermore, when an arbitrary position on the tomographic image TM is designated by the input unit 4, the control unit 20 can additionally display a second frame K and can change the size of the second frame K2 similarly to the first frame K1 (refer to FIG. 4). Here, the second frame K2 is set to be located at a position different from that of the first frame K1 in the tomographic image TM.

Then, the control unit 20 sets the second area set via the input unit 4 as a second analysis region. That is, the second analysis region is set by the frame K2. Then, similar to the first analysis result AN1, the control unit 20 displays a second analysis result AN2 relating to the second analysis region, on the tomographic image TM.

That is, the control unit 20 can set multiple analysis regions on the tomographic image TM. Then, the control unit 20 can simultaneously display the first analysis result AN1 and the second analysis result AN2 on the display unit 1. Accordingly, for example, the examiner can compare multiple analysis results relating to different analysis regions on the same tomographic image. That is, since it is possible to determine any multiple locations, a scope of diagnosis is broadened. Therefore, it is possible to improve diagnostic efficiency.

The control unit 20 may perform an integrated analysis on the first analysis result AN1 and the second analysis result AN2, and may display an integrated analysis result AN1 on the display unit 1. For example, the control unit 20 may calculate at least one of a ratio or a difference between the first analysis result AN1 and the second analysis result AN2, and may display the calculation result on the display unit 1.

Outputting the integrated analysis result relating to the multiple analysis regions is advantageous, for example, when determining the symmetricity of two analysis results. For example, the thickness of the retinal layer influenced by glaucoma is changed asymmetrically in an upper side region and a lower side region of the eye fundus. The upper side region and the lower side region are divided, for example, by a stream of the nerve fiber layer connecting the fovea centralis and the papilla (alternatively, a forming position of the fovea centralis or the papilla). Then, the examiner can easily evaluate the symmetricity of the retinal thicknesses by comparing and analyzing the analysis results between the vertically divided analysis regions.

Therefore, it is particularly advantageous when analyzing the tomographic image acquired by setting the transverse direction (scanning line) of the measurement light on the eye fundus of the subject eye to be vertical to the eye fundus. Specifically, the transverse position may be orthogonal to a laterally extending center line defined by the stream of the nerve fiber layer connecting the fovea centralis and the papilla (alternatively, a forming position of the fovea centralis or the papilla in the vertical direction), and the transverse position.

In addition, as described above, the control unit 20 can set multiple regions separated from each other on the tomographic image as multiple analysis regions. Accordingly, for example, the analysis results relating to the separated region on the eye fundus can be respectively output. Accordingly, it is possible to more specifically compare the abnormal site with a side located at the symmetric position of the abnormal site. In particular, this is advantageous since it is said that there is a change in the thickness in a certain region from the fovea centralis.

<Analysis of Symmetricity in Two Analysis Regions>

Hereinafter, a setting method for performing a smooth setting operation when determining the symmetricity between the first analysis region and the second analysis region will be described as an example.

For example, as shown in FIGS. 5 and 6, the control unit 20 may set a position of the second analysis region based on a position of the first analysis region and the reference position which are set on the tomographic image. Accordingly, for example, it is possible to reduce the effort of setting the second analysis region, and to reliably set the analysis region which is symmetric with respect to the set center position.

The control unit 20 sets the first analysis region based on the position of the frame K1 set by the examiner. The control unit 20 displays a center line C to be superimposed on the tomographic image TM. The control unit 20 receives the operation signal from the input unit 4, and adjusts the display position of the center line C on the tomographic image TM. The orientation of the center line C on the tomographic image TM may be configured to be adjustable.

Then, the position adjustment is completed by arranging the center line C in the characteristic site (for example, the fovea centralis, the papilla or the like) on the tomographic image TM. The control unit 20 sets the center position based on the position of the center line C.

Based on the position of the first analysis region and the center position, the control unit 20 sets the second analysis region in a region symmetric to the first analysis region with respect to the center position. Then, the control unit 20 additionally displays the second frame K2 indicating the second analysis region on the tomographic image TM. Here, it is preferable that the frame K2 have a size which is the same as that of the first frame K1. This is because it is possible to accurately determine the symmetricity if both frames have the same size.

Then, the control unit 20 simultaneously displays the first analysis result AN1 relating to the first analysis region and the second analysis result AN2 relating to the second analysis region, on the display unit 1. Furthermore, the control unit 20 may display the integrated analysis result based on the first analysis result and the second analysis result, on the display unit 1. In the above description, the examiner manually sets the first analysis region and the center position. However, the present disclosure is not limited thereto.

When a display position of one of the first frame K1 and the second frame K2 is adjusted with respect to the center position, the control unit 20 may adjust a display position of the other of the first frame K1 and the second frame K2 to be symmetric to the display position of the frame of the one of the first frame K1 and the second frame K2 and the center position.

<Setting of Multiple Analysis Regions by Dividing Analysis Region>

In the above, there has been described the case where the multiple analysis regions separated from each other are set. However, the present disclosure is not limited thereto. For example, when the size and the display position of the frames K are adjusted by the operation of the examiner, as shown in FIG. 7, the control unit 20 may be configured to set one location of an arbitrary analysis region on the tomographic image TM and set multiple analysis regions by dividing the set analysis region. In this case, the dividing direction may be arbitrarily set to be the depth direction, the transverse direction or the oblique direction on the tomographic image.

When the analysis region is set, the control unit 20 displays the center line C to be superimposed on the tomographic image TM at a position corresponding to the center of the set analysis region. The center line C divides the analysis region in the scanning direction on the tomographic image TM. The control unit 20 can adjust the position of the center line C on the analysis region by receiving the operation signal from the input unit 4. The control unit 20 collectively moves the center line C and each analysis region (frame K) in response to the movement of the center line C.

Then, the position adjustment is completed by arranging the center line C in the characteristic site (for example, the fovea centralis, the papilla or the like) on the tomographic image TM. The control unit 20 sets the center position based on the position of the center line C. Based on a positional relationship between the analysis region and the center position, the control unit 20 sets one analysis region divided by the center line C as the first analysis region, and sets the other analysis region as the second analysis region.

The control unit 20 simultaneously displays the first analysis result AN1 relating to the first analysis region and the second analysis result AN2 relating to the second analysis region, on the display unit 1. Further, the control unit 20 may display the integrated analysis result AN1 based on the first analysis result and the second analysis result, on the display unit 1.

When the display position of one frame divided by the center line C is adjusted with respect to the center position, the control unit 20 may adjust the display position of the other divided frame to be symmetric to the display position of one frame K with respect to the center position.

In the above description, the center position is manually set by the examiner. However, the present disclosure is not limited thereto. When automatically setting the center line C, for example, the center line C may be automatically determined by using positional information of at least any one of the fovea centralis and the papilla which are detected by image processing. Therefore, the control unit 20 detects the positional information of the characteristic site (for example, the fovea centralis and the papilla) in the tomographic image TM by image processing. Then, the control unit 20 sets the center line C based on the positional information of the detected characteristic site.

The fovea centralis is a portion having the thinnest retinal thickness. Accordingly, for example, the position of the fovea centralis can be detected by comparing the retinal thicknesses at each position in the tomographic image. In addition, since the papilla has no RPE layer, the position of the papilla can be detected by analyzing presence or absence of the RPE layer at each position of the tomographic image.

In addition, indirect position detection may be performed so as to define the position separated from a certain site (for example, the fovea centralis) by a certain distance in a certain direction, as the characteristic site (for example, the position of the papilla). In addition, the CPU 20 may detect the position of the characteristic site by associating the examination result of the perimeter or the analysis result of the front image captured by the eye fundus camera or the SLO, with the tomographic image.

When using the perimeter, the control unit 20 detects, for example, the most sensitive position as the fovea centralis, and associates the detected position with the tomographic image. Further, the control unit 20 detects, for example, an abnormal site in the visual field, and associates the detected position with the tomographic image. When using the front image, the control unit 20 detects, for example, the position corresponding to the fovea centralis and the papilla on the front image, and associates the detected position and the tomographic image.

<Parameter of Analysis Region>

In the above description, a parameter (for example, at least any one of the size and the position) when setting the analysis region may be fixed in advance. Hereinafter, an example thereof will be described.

<Fixed Size of Analysis Region>

In the above description, the size of the analysis region can be arbitrarily adjusted. However, the present disclosure is not limited thereto.

Figure 8:
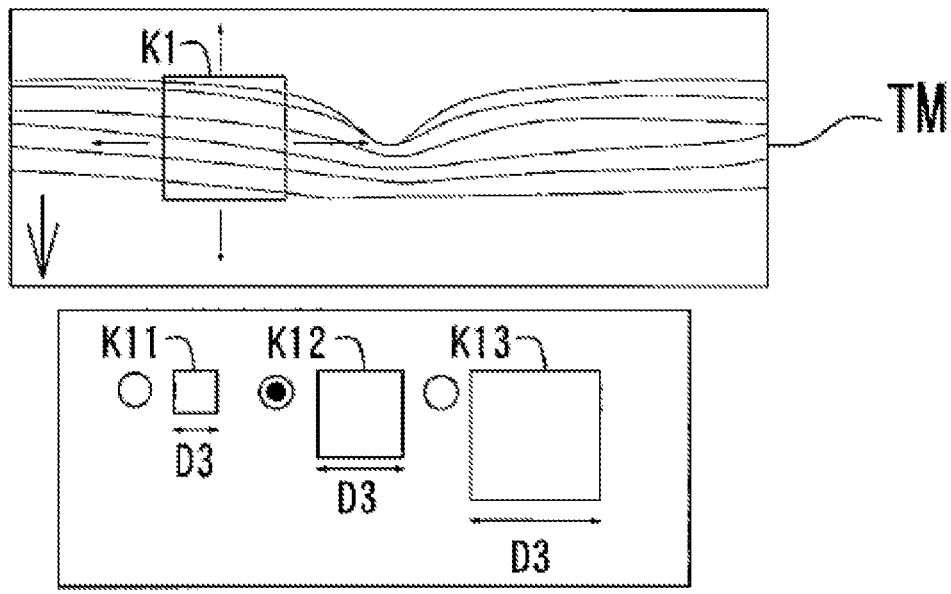
FIG. 8 shows an example when a size of the analysis region is fixed.

FIG. 8 shows an example of when the size of the analysis region is fixed. The frame K1 has a certain width in the vertical and horizontal directions to have a fixed size in the vertical and horizontal directions. The size of the frame K1 can be set in advance by a numerical input. Here, the frame K1 is used in setting an arbitrary area (two-dimensional region) on the OCT data so as to have a pre-set size.

In this example, multiple sizes of the analysis region may be prepared and a specific size may be selectable from the multiple sizes. For example, the control unit 20 displays in advance multiple frames K1 (for example, frames K11, K12 and K13) respectively having different sizes, on the display unit 1.

The control unit 20 receives the selection instruction for selecting one pattern from multiple patterns displayed in advance. The control unit 20 displays the frame K1 (for example, the frame K12) which has the same size as that of the selected frame, to be superimposed on the tomographic image TM. The control unit 20 can adjust the position of the frame K1 (for example, the frame K12) on the tomographic image TM by receiving the operation signal from the input unit 4. If the first analysis region is set by the frame K1, the control unit 20 displays the analysis result corresponding to the frame K1, on the display unit 1.

Furthermore, the control unit 20 may be configured to additionally display the frame K2 having the same size as that of the analysis region set in advance, on the display unit 1. Then, the control unit 20 simultaneously displays the analysis result corresponding to the frame K1 and the analysis result corresponding to the frame K2, on the display unit 1. Furthermore, the control unit 20 displays the integrated analysis result based on each analysis result, on the display unit 1. Accordingly, for example, it is possible to output the analysis result relating to the multiple analysis regions which have a fixed size desired by the examiner.

<Fixed Position of Analysis Region>

Figure 9:
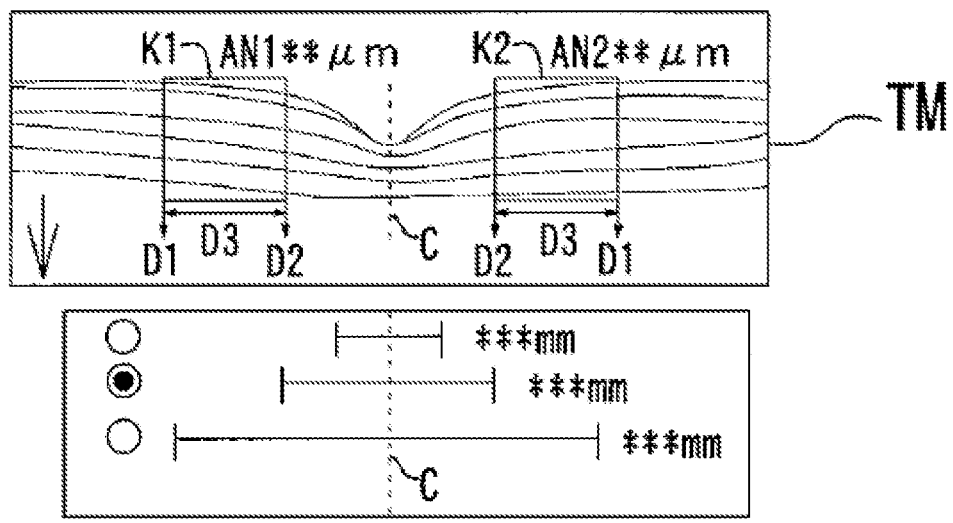
FIG. 9 shows an example when a position of the analysis region is fixed.

FIG. 9 shows an example of when the position of the analysis region is fixed. In a case of FIG. 9, the frames K1 and K2 have a certain width in the vertical and horizontal directions, and are set to have an equal distance with respect to the center line C. The distance from the center line C can be set in advance by the numeric input. Here, the frames K1 and K2 are used in setting an area (two-dimensional region) defined to be separated from the reference position (for example, the center position) by a pre-set distance on the tomographic image.

In this example, multiple distances from the reference position to the analysis region may be prepared and a specific distance may be selectable from the multiple distances (refer to FIG. 9). For example, the control unit 20 displays the multiple distances on the display unit 1 in advance.

The control unit 20 receives the selection instruction for selecting one distance from multiple distances displayed in advance. The control unit 20 displays the center line C to be superimposed on the tomographic image TM, and displays the frames K1 and K2 at the position separated from the center line C by the selected distance. The control unit 20 can adjust the position of the center line C by receiving the operation signal from the input unit 4. If the center line C is moved, the control unit 20 moves the frames K1 and K2 by the selected distance while maintaining the distance from the center line C. That is, the control unit 20 can move the pattern formed from the center line C and the frames K1 and K2 onto the display unit 1 by receiving the operation signal from the examiner.

Then, the position adjustment is completed by arranging the center line C in the characteristic site (for example, the fovea centralis and the papilla) on the tomographic image TM. The control unit 20 sets the center position based on the position of the center line C.

Based on the positional relationship between the analysis region and the center position, the control unit 20 sets one region separated from the center position by the distance selected in advance as the first analysis region, and sets the other region as the second analysis region.

The control unit 20 simultaneously displays the first analysis result AN1 relating to the first analysis region and the second analysis result AN2 relating to the second analysis region, on the display unit 1. Furthermore, the control unit 20 may display the integrated analysis result based on the first analysis result and the second analysis result, on the display unit 1.

<Display Size of Frame K>

The display size of the frames K, K1 and K2 may be set to correspond to the actual dimensions on the eye fundus of the subject eye. For example, the control unit 20 may fix the size of the analysis region to correspond to the actual dimensions, and may change the display size of the frame K based on the actual dimensions on the eye fundus of the subject eye. The actual dimensions on the eye fundus are obtained by optical calculation based on an eye axial length of the subject eye, eye refractive power, a shape of the cornea and the like.

<Shape of Analysis Region>

In the above description, as a shape of the analysis region, the rectangular shape has been described as an example. However, the present disclosure is not limited thereto. For example, the shape may be a point or a line. Alternatively, the shape may be any other shape (a circular shape, a triangular shape or the like).

<Case of Setting Multiple Analysis Regions in Area Other Than Tomographic Image>

In the above description, the setting method of the analysis region on the tomographic image TM has been described. However, the present disclosure is not limited thereto. For example, the control unit 20 may be configured to set multiple analysis regions on at least any one of the two-dimensional front image, the retinal thickness graph, the thickness map, the two-dimensional analysis chart, and the two-dimensional analysis map. The control unit 20 simultaneously displays the first analysis result AN1 relating to the first analysis region and the second analysis result AN2 relating to the second analysis region, on the display unit 1. Further, the control unit 20 may display the integrated analysis result based on the first analysis result and the second analysis result, on the display unit 1.

The two-dimensional analysis map and the two-dimensional analysis chart are calculated based on the three-dimensional OCT data. For example, the three-dimensional OCT data is formed from the tomographic image in each scanning line which is acquired by the two-dimensional scan (for example, raster scan) of the measurement beam. Then, the two-dimensional analysis map is formed by performing the analysis process on each tomographic image of the three-dimensional OCT data. Of course, the two-dimensional analysis map may be calculated, based on each OCT data acquired by the multi-scan such as the radial scan.

<Creation of Time-Series Graph>

The control unit 20 may output a time-series graph 150 by using the analysis result relating to the multiple analysis regions set as described above (refer to FIG. 10).

For example, the control unit 20 sets multiple regions set via the input unit 4 as graph creation regions. After the multiple regions are set in the tomographic image TM by the frames K1 and K2, regions are set at the same position on the other tomographic images which are acquired on different days, and are set as graph creation regions. That is, the control unit 20 reflects the regions set on a certain tomographic image TM on the other images. Accordingly, a region selected by the examiner on the tomographic image acquired on each examination date is set as the graph creation region. The same position is not necessarily a completely identical position. It is sufficient if the level of observation can be regarded as being at substantially the same position which enables the follow-up observation. The control unit 20 stores the position of the graph creation region in the storage unit 30, thereby facilitating the follow-up observation at the same position.

The control unit 20 acquires respective multiple layer thickness data in the regions set by the frames K1 and K2 in the layer thickness data of the subject eye which relates to each examination date. The control unit 20 creates the time-series graph formed from the layer thickness data acquired on each examination date, and outputs the created time-series graph 150 onto the display unit 1.

The control unit 20 calculates a basic statistical value (for example, a representative value and a degree of dispersion) of each layer thickness data inside the regions. The control unit 20 creates the time-series graph formed from the basic statistical value of the layer thickness data acquired on each examination date, and outputs the created time-series graph 150 onto the display unit 1. The time-series graph 150 displays a time-series graph 160 of the first analysis result relating to the first analysis region and a time-series graph 170 of the second analysis result relating to the second analysis region, on the same graph.

Accordingly, for example, it is possible to output the time-series graph corresponding to the multiple regions to which the examiner pays attention on the tomographic image. Therefore, the examiner can easily perform the follow-up observation on the layer thickness data corresponding to a position which the examiner desires to examine.

When outputting the time-series graph 150, the control unit 20 may output a time-series graph 180 of the integrated analysis result of the first analysis result and the second analysis result.

Hereinafter, setting of the analysis region on the two-dimensional front image and a setting method of the analysis region in the two-dimensional analysis map will be described as an example.

<Setting on Two-Dimensional Front Image>

Figure 11:
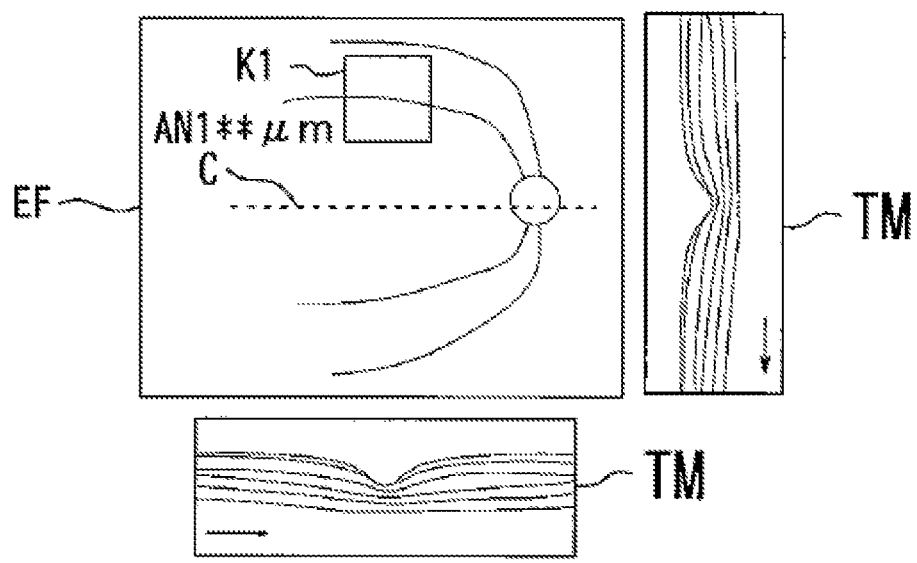
FIG. 11 is a first view showing an example when setting an analysis region of OCT data on a two-dimensional front image.
Figure 12:
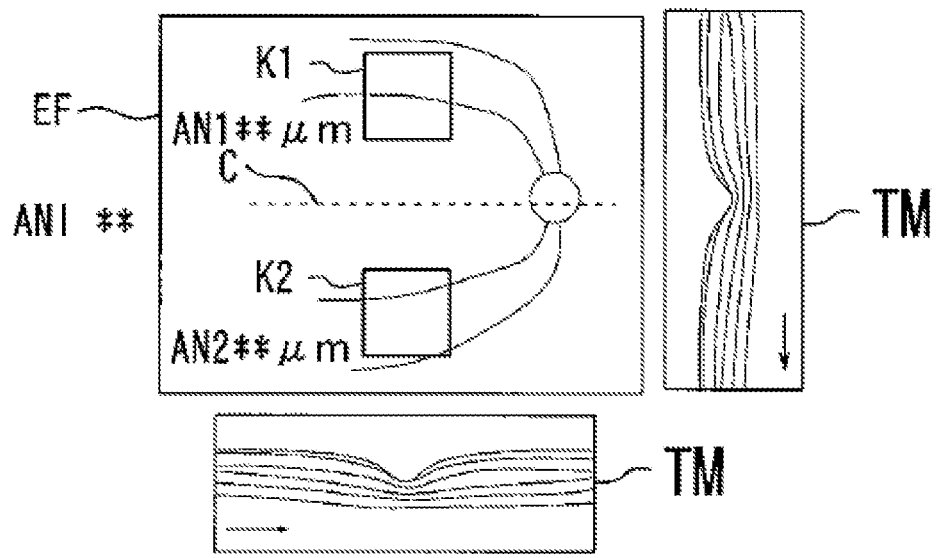
FIG. 12 is a second view showing an example when setting an analysis region of OCT data on a two-dimensional front image.
Figure 13:
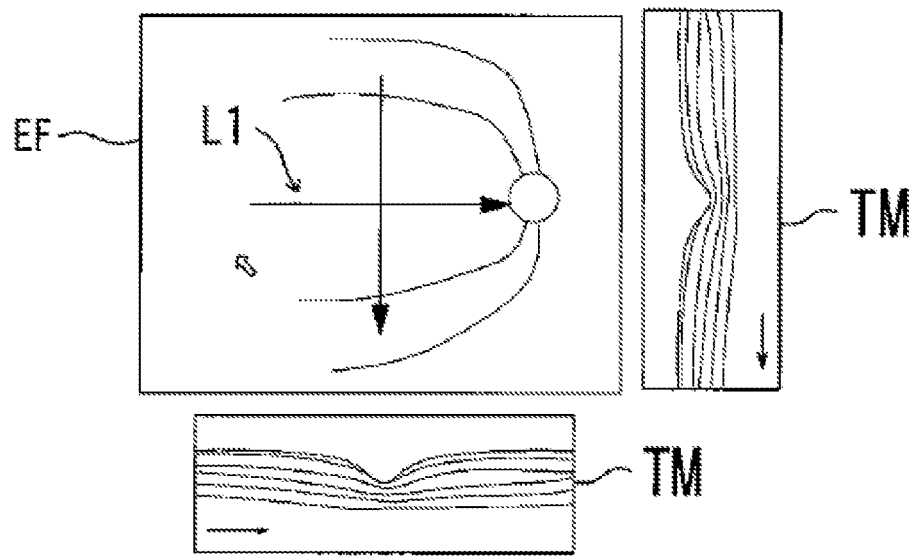
FIG. 13 is a third view showing an example when setting an analysis region of OCT data on a two-dimensional front image.

FIGS. 11 and 12 show an example when setting the analysis region of OCT data on the two-dimensional front image. The control unit 20 displays a front image EF on the display unit 1. For example, the front image EF can adopt a two-dimensional front image or the like which is generated from an interference signal of the OCT in addition to the SLO or the eye fundus camera image. In the front image EF, a position thereof is associated with three-dimensional OCT data in advance. Accordingly, if the analysis region is set on the front image EF, the control unit 20 displays at least a portion of the tomographic image corresponding to the set analysis region in the three-dimensional OCT data, on the display unit 1. Then, the control unit 20 simultaneously displays the analysis result corresponding to the set analysis region, on the display unit 1. It is preferable that the tomographic image corresponding to a setting line L1 be displayed in parallel with the front image EF. Accordingly, for example, identification of a target region is facilitated. The control unit 20 adjusts the display position of the setting line L1 on the front image EF by receiving the operation signal from the input unit 4. Then, the control unit 20 displays the tomographic image corresponding to the display position of the setting line L1, on the display unit 1 (refer to FIG. 13). The control unit 20 may be configured to delete the setting line L1 when setting the analysis region.

For example, the control unit 20 sets the first analysis region based on the position of the frame K1 set by the examiner on the front image EF (refer to FIG. 11). The control unit 20 displays the center line C to be superimposed on the front image EF. The control unit 20 adjusts the display position of the center line C on the front image EF by receiving the operation signal from the input unit 4. The control unit 20 may be configured to adjust the orientation of the center line C on the front image EF.

Then, the position adjustment is completed by arranging the center line C in the characteristic site (for example, the fovea centralis, the papilla or the like) on the front image EF. The control unit 20 sets the center position based on the position of the center line C. Based on the position of the first analysis region and the center position, the control unit 20 sets the second analysis region in a region symmetric to the first analysis region with respect to the center position on the front image EF (refer to FIG. 12). Then, the control unit 20 additionally displays the second frame K2 indicating the second analysis region on the front image EF. Here, it is preferable that the frame K2 have the same size as that of the first frame K1.

The control unit 20 acquires the tomographic image corresponding to the first analysis region and the second analysis region from the three-dimensional OCT data. In addition, the control unit 20 simultaneously displays the first analysis result AN1 relating to the first analysis region and the second analysis result AN2 relating to the second analysis region, on the display unit 1. Further, the control unit 20 displays the integrated analysis result AN1 based on the first analysis result AN1 and the second analysis result AN2, on the display unit 1.

For example, the control unit 20 acquires each layer thickness data based on the OCT data inside the region which is set by the first frame K1 or the second frame K2. Then, the control unit 20 calculates the basic statistical value (for example, the representative value and the degree of dispersion) of each layer thickness data in the region. The control unit 20 displays the calculated basic statistical value on the display unit 1 (for example, displays the value to be superimposed on the front image EF).

When acquiring each layer thickness data based on the OCT data, the control unit 20 may acquire each layer thickness data by analyzing the tomographic image in each analysis region through image processing. In addition, the layer thickness data in each position of the three-dimensional OCT data may be stored in the memory 74 in advance, and the control unit 20 may acquire the layer thickness data in each analysis region from the memory 74. Further, as the integrated analysis result, the control unit 20 may display a ratio or a difference of the basic statistical value in each analysis region, on the display unit 1.

Accordingly, for example, it is possible to set the multiple analysis regions on the two-dimensional front image. For example, if a target site (for example, an abnormal site) is identified in the front image, the examiner can easily compare the analysis result in the target site with the analysis result in the other sites. A setting method on the two-dimensional front image is not limited to the above-described example. For example, as the setting method on the tomographic image, the above-described setting method for the multiple regions can be used. Further, the control unit 20 may create the time-series graph based on the analysis result (refer to FIG. 10).

<Setting on Two-Dimensional Analysis Map>

Figure 14:
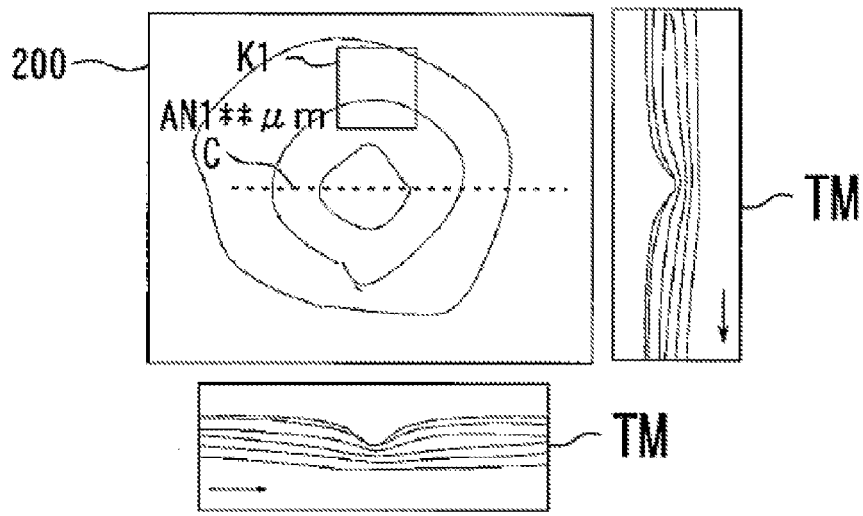
FIG. 14 is a first view showing an example when setting an analysis region of OCT data on a two-dimensional analysis map.
Figure 15:
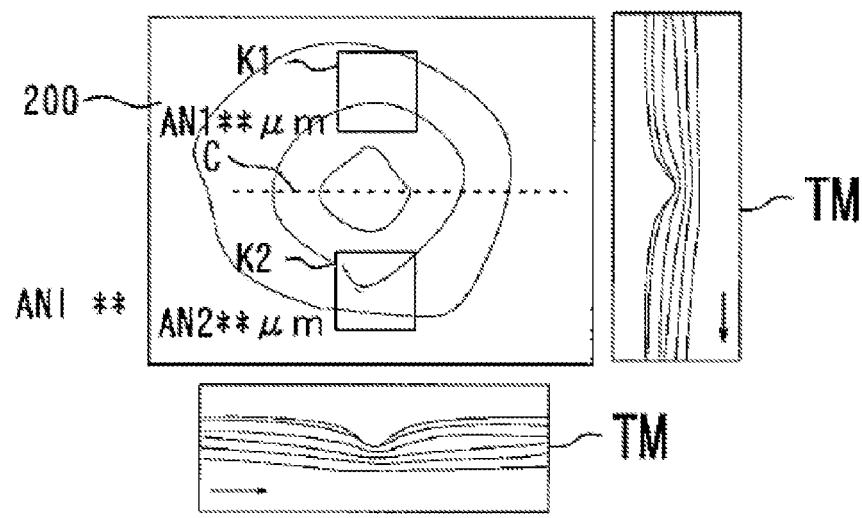
FIG. 15 is a second view showing an example when setting an analysis region of OCT data on a two-dimensional analysis map.
Figure 16:
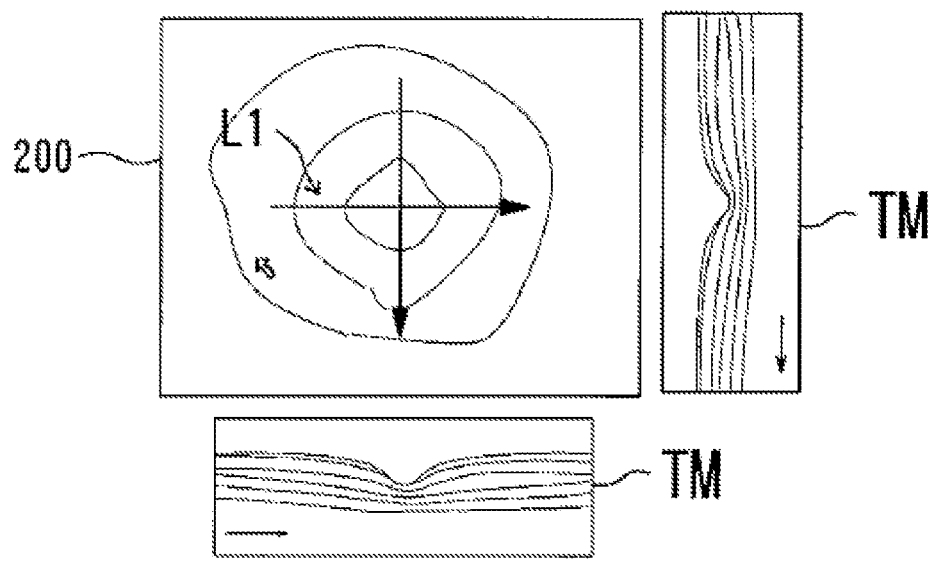
FIG. 16 is a third view showing an example when setting an analysis region of OCT data on a two-dimensional analysis map.

FIGS. 14 and 15 show an example when setting the analysis region of the OCT data on the two-dimensional analysis map. The control unit 20 displays an analysis map 200 on the display unit 1. The analysis map 200 may be displayed to be superimposed on the front image EF. For example, the analysis map 200 includes a retinal thickness map, a choroidal thickness map and the like. It is preferable that the tomographic image corresponding to the setting line L1 be displayed in parallel with the analysis map 200. Accordingly, for example, identification of the target region is facilitated. The control unit 20 adjusts the display position of the setting line L1 on the front image EF by receiving the operation signal from the input unit 4. Then, the control unit 20 displays the tomographic image corresponding to the display position of the setting line L1, on the display unit 1 (refer to FIG. 16). The control unit 20 may delete the setting line L1 when setting the analysis region.

The retinal thickness map is a color map showing two-dimensional distribution of the retinal thickness of the subject eye, and is classified by colors according to the layer thickness. The retinal thickness map includes a thickness map, a comparison map, a deviation map, and an examination date comparison thickness difference map.

The thickness map indicates the thickness of the retinal layer. The comparison map indicates a comparison result between the thickness of the retinal layer of the subject eye and the thickness of the retinal layer of a normal eye stored in the normal eye database. The deviation map uses standard deviation to indicate deviation between the thickness of the retinal layer of the subject eye and the thickness of the retinal layer of the normal eye stored in the normal eye database. The examination date comparison thickness difference map indicates the difference in the thickness on each examination date.

With regard to the analysis map 200, the analysis result (for example, layer thickness data) at each position which is acquired by analyzing the three-dimensional OCT data is associated with the position on the map. Accordingly, if the analysis region is set on the analysis map 200, the control unit 20 acquires the analysis result (for example, layer thickness data) relating to the set analysis region. The control unit 20 displays the acquired analysis result on the display unit 1.

For example, the control unit 20 sets the first analysis region in the analysis map 200, based on the position of the frame K1 set by the examiner. The control unit 20 displays the center line C to be superimposed on the front image EF. The control unit 20 adjusts the display position of the center line C on the analysis map 200 by receiving the operation signal from the input unit 4. The control unit 20 may be configured to adjust the orientation of the center line C on the analysis map 200.

Then, the position adjustment is completed by arranging the center line C in the target site (for example, a position corresponding to the fovea centralis and the papilla, the abnormal site or the like on the analysis map 200) on the analysis map 200. The control unit 20 sets the center position based on the position of the center line C. Based on the position of the first analysis region and the center position, the control unit 20 sets the second analysis region in a region symmetric to the first analysis region with respect to the center position on the analysis map 200. Then, the control unit 20 additionally displays the second frame K2 indicating the second analysis region on the analysis map 200. Here, it is preferable that the frame K2 have the same size as that of the first frame K1.

The control unit 20 simultaneously displays the first analysis result AN1 relating to the first analysis region and the second analysis result AN2 relating to the second analysis region, on the display unit 1. Furthermore, the control unit 20 displays the integrated analysis result AN1 based on the first analysis result and the second analysis result, on the display unit 1.

For example, the control unit 20 acquires each layer thickness data in the region set by the first frame K1 or the second frame K2. Then, the control unit 20 calculates the basic statistical value (for example, the representative value and the degree of dispersion) of each layer thickness data in the region. The control unit 20 displays the calculated basic statistical value on the display unit 1 (for example, displays the value to be superimposed on the analysis map 200). In addition, as the integrated analysis result, the control unit 20 displays a ratio or a difference of the basic statistical value in each analysis region, on the display unit 1.

Accordingly, for example, it is possible to set the multiple analysis regions on the analysis map 200. For example, if a target site (for example, an abnormal site) is identified in the analysis map, the examiner can easily compare the analysis result in the target site with the analysis result in the other sites.

A setting method on the analysis map 200 is not limited to the above-described example. For example, as the setting method on the tomographic image, the above-described setting method for the multiple regions can be used. In addition, the control unit 20 may create the time-series graph based on the analysis result (refer to FIG. 10).

What is claimed is:

1. An ophthalmic analysis apparatus configured to acquire an analysis result of a tomographic image of a subject eye which is acquired by using optical coherence tomography (OCT), and to output the analysis result, the ophthalmic analysis apparatus comprising:
    a processor; and
    a memory storing computer readable instructions, when executed by the processor, causing the ophthalmic analysis apparatus to function as:
        a display control unit configured to control a display unit to display a two-dimensional image which is one of an OCT tomographic image, a two-dimensional front image whose position is associated with three-dimensional OCT data formed from an OCT tomographic image in each line, a two-dimensional analysis map which is calculated based on three-dimensional OCT data formed from an OCT tomographic image in each line, and a two-dimensional analysis chart which is calculated based on three-dimensional OCT data formed from an OCT tomographic image in each line;
        an analysis region setting unit configured to set multiple analysis regions on the two-dimensional image displayed on the display unit by the display control unit; and
        an output control unit configured to acquire an analysis result in the multiple analysis regions set by the analysis region setting unit and to output the acquired analysis result; and
    wherein the analysis result is an integrated analysis result by calculating ratios or differences between analysis results for each of the set multiple analysis regions.

2. The ophthalmic analysis apparatus according to claim 1, wherein the memory further stores computer readable instructions, when executed by the processor, causing the ophthalmic analysis apparatus to function as an instruction receiving unit configured to receive a setting instruction from an examiner to set the multiple analysis regions, and
    wherein the analysis region setting unit is configured to set the multiple analysis regions on the two-dimensional image according to the setting instruction received by the instruction receiving unit.

3. The ophthalmic analysis apparatus according to claim 2, wherein the two-dimensional image is the two-dimensional analysis map,
    wherein the analysis region setting unit is configured to adjust a position or an orientation of a center line on the two-dimensional analysis map, according to the setting instruction received by the instruction receiving unit, and
    wherein the analysis region setting unit is configured to set a first analysis region and a second analysis region which are symmetric with respect to the center line.

4. The ophthalmic analysis apparatus according to claim 1, wherein the analysis region setting unit is configured to set a reference position on the two-dimensional image between the multiple analysis regions to be set, and to set a first analysis region and a second analysis region based on the reference position.

5. The ophthalmic analysis apparatus according to claim 4, wherein the analysis region setting unit is configured to, when a position of one of the first analysis region and the second analysis region is changed with respect to the reference position, change a position of the other of the first analysis region and the second analysis region with respect to the reference position.

6. The ophthalmic analysis apparatus according to claim 1, wherein the analysis region setting unit is configured to set a reference position on the two-dimensional image between the multiple analysis regions to be set, and to set a position of a second analysis region based on a position of a first analysis region and the reference position.

7. The ophthalmic analysis apparatus according to claim 1, wherein the analysis region setting unit is configured to set a reference position on the two-dimensional image between the multiple analysis regions to be set, and to divide a pre-set analysis region with respect to the reference position to set the divided analysis regions as a first analysis region and a second analysis region.

8. The ophthalmic analysis apparatus according to claim 1, wherein the analysis region setting unit is configured to set a reference position on the two-dimensional image between the multiple analysis regions to be set, and to set a first analysis region and a second analysis region which are symmetric to each other with respect to the reference position.

9. The ophthalmic analysis apparatus according to claim 1, wherein the memory further stores instructions, when executed by the processor, causing the ophthalmic analysis apparatus to function as a characteristic site detection unit configured to detect a position of a characteristic site in the two-dimensional image, and
    wherein the analysis region setting unit is configured to set positions of the multiple analysis regions on the two-dimensional image based on the position of the characteristic site detected by the characteristic site detection unit.

10. The ophthalmic analysis apparatus according to claim 1, wherein the analysis region setting unit is configured to change at least one of a position, a size and a shape of the analysis regions on the two-dimensional image.

11. The ophthalmic analysis apparatus according to claim 1, wherein the analysis region setting unit is configured to pre-set at least one of a position and a size of the analysis regions on the two-dimensional image, and to set the multiple analysis regions at the pre-set position and/or in the pre-set size.

12. The ophthalmic analysis apparatus according to claim 1, wherein each of the multiple analysis regions has a same size.

13. The ophthalmic analysis apparatus according to claim 1, wherein the output control unit is configured to calculate a basic statistical value of layer thickness data in the multiple analysis regions set by the analysis region setting unit, and to output the calculated basic statistical value as the analysis result.

14. The ophthalmic analysis apparatus according to claim 1,
wherein the output control unit is configured to calculate a basic statistical value of layer thickness data in the multiple analysis regions set by the analysis region setting unit, and to output a ratio or a difference of the basic statistical value in each of the analysis regions as the analysis result.

15. The ophthalmic analysis apparatus according to claim 1, wherein each of the analysis regions are set at positions that are symmetric with respect to a reference position.

16. An ophthalmic analysis apparatus configured to acquire an analysis result of a tomographic image of a subject eye which is acquired by using optical coherence tomography (OCT), and to output the analysis result, the ophthalmic analysis apparatus comprising:
   a processor; and
   a memory storing computer readable instructions, when executed by the processor, causing the ophthalmic analysis apparatus to function as:
      a display control unit configured to control a display unit to display a two-dimensional image which is one of an OCT tomographic image, a two-dimensional front image whose position is associated with three-dimensional OCT data formed from an OCT tomographic image in each line, a two-dimensional analysis map which is calculated based on three-dimensional OCT data formed from an OCT tomographic image in each line, and a two-dimensional analysis chart which is calculated based on three-dimensional OCT data formed from an OCT tomographic image in each line;
      an analysis region setting unit configured to set multiple analysis regions on the two-dimensional image displayed on the display unit by the display control unit; and
      an output control unit configured to acquire an analysis result in the multiple analysis regions set by the analysis region setting unit and to output the acquired analysis result;
   wherein the memory further stores instructions, when executed by the processor, causing the ophthalmic analysis apparatus to function as a characteristic site detection unit configured to detect a position of a fovea centralis and a position of a papilla in the two-dimensional image, and
   wherein the analysis region setting unit is configured to set a center line based on the position of the fovea centralis and the position of the papilla which are detected by the characteristic site detection unit, and to set a first analysis region and a second analysis region to be symmetric with respect to the center line.

17. A non-transitory computer-readable medium having a computer program stored thereon and readable by a computer configured to acquire an analysis result of a tomographic image of a subject eye which is acquired by using optical coherence tomography (OCT), the computer program, when executed by the computer, causing the computer to perform operations comprising:
   controlling a display unit to display a two-dimensional image which is one of an OCT tomographic image, a two-dimensional front image whose position is associated with three-dimensional OCT data formed from an OCT tomographic image in each line, a two-dimensional analysis map which is calculated based on three-dimensional OCT data formed from an OCT tomographic image in each line, and a two-dimensional analysis chart which is calculated based on three-dimensional OCT data formed from an OCT tomographic image in each line;
   setting multiple analysis regions on the two-dimensional image displayed on the display unit by the display control unit; and
   acquiring an analysis result in the multiple analysis regions set by the analysis region setting unit and outputting the acquired analysis result; and
   wherein the analysis result is an integrated analysis result by calculating ratios or differences between analysis results for each of the set multiple analysis regions.

* * * * *